US012723058B2

(12) United States Patent
Lee et al.

(10) Patent No.: US 12,723,058 B2
(45) Date of Patent: Sep. 1, 2026

(54) PROCESSES FOR PREPARING CONJUGATES OF THE IL-2 PROTEIN

(71) Applicant: Merck Sharp & Dohme LLC, Rahway, NJ (US)

(72) Inventors: Joshua Lee, Parlin, NJ (US); Gregory F. Pirrone, Springfield, NJ (US); Michael J. Iammarino, Manalapan, NJ (US); David J. Roush, Colts Neck, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 895 days.

(21) Appl. No.: 17/998,725

(22) PCT Filed: May 17, 2021

(86) PCT No.: PCT/US2021/032662

§ 371 (c)(1),
(2) Date: Nov. 14, 2022

(87) PCT Pub. No.: WO2021/236474

PCT Pub. Date: Nov. 25, 2021

(65) Prior Publication Data

US 2023/0272001 A1 Aug. 31, 2023

Related U.S. Application Data

(60) Provisional application No. 63/029,189, filed on May 22, 2020.

(51) Int. Cl.

| | |
|---|---|
| ***A61K 47/60*** | (2017.01) |
| ***A61K 47/68*** | (2017.01) |
| ***C07C 13/567*** | (2006.01) |
| ***C07K 1/00*** | (2006.01) |

(52) U.S. Cl.

CPC ................ *C07K 1/00* (2013.01); *A61K 47/60* (2017.08); *A61K 47/6813* (2017.08); *C07C 13/567* (2013.01); *C07C 2603/18* (2017.05)

(58) Field of Classification Search

CPC ...... C07K 1/00; A61K 47/60; A61K 47/6813; A61K 38/2013; C07C 13/567; C07C 2603/18

See application file for complete search history.

(56) References Cited

U.S. PATENT DOCUMENTS

| | | | | |
|---|---|---|---|---|
| 4,766,106 | A | 8/1988 | Katre et al. | |
| 4,902,502 | A | 2/1990 | Nitecki et al. | |
| 5,089,261 | A | 2/1992 | Nitecki et al. | |
| 5,116,943 | A | 5/1992 | Koths et al. | |
| 5,153,310 | A | 10/1992 | Mitchell et al. | |
| 5,206,344 | A | 4/1993 | Katre et al. | |
| 5,635,597 | A | 6/1997 | Barrett et al. | |
| 7,101,965 | B2 | 9/2006 | Theze et al. | |
| 7,567,215 | B1 | 7/2009 | All et al. | |
| 9,861,705 | B2 | 1/2018 | Bossard et al. | |
| 2004/0126361 | A1 | 7/2004 | Saifer et al. | |
| 2004/0175337 | A1 | 9/2004 | Richard et al. | |
| 2008/0234193 | A1 * | 9/2008 | Bossard .................... | A61P 7/00 514/17.2 |
| 2010/0036097 | A1 | 2/2010 | Wittrup et al. | |
| 2018/0092898 | A1 | 4/2018 | Bio et al. | |

FOREIGN PATENT DOCUMENTS

| | | | | |
|---|---|---|---|---|
| WO | 2019226538 A1 | | 11/2019 | |
| WO | WO-2020056066 A1 | * | 3/2020 | ............ C07K 14/55 |

* cited by examiner

*Primary Examiner* — Kumar R Bhushan

(74) *Attorney, Agent, or Firm* — John David Reilly; John C. Todaro

(57) ABSTRACT

Disclosed herein are novel processes for preparing IL-2 conjugates with one or more water-soluble polymers. In one embodiment, the IL-2 conjugate comprises five poly(ethylene glycol) polymers each of which is covalently attached to the IL-2 moiety via a releasable linkage to an amino group of the IL-2 moiety.

3 Claims, 4 Drawing Sheets

Specification includes a Sequence Listing.

IL-2 SEQ ID No.1

```
        10         20         30         40         50         60
PTSSSTKKTQ LQLEHLLLDL QMILNGINNY KNPKLTRMLT FKFYMPKKAT ELKHLQCLEE
        70         80         90        100        110        120
ELKPLEEVLN LAQSKNFHLR PRDLISNINV IVLELKGSET TFMCEYADET ATIVEFLNRW
       130
ITFSQSIIST LT
```

FIG. 1

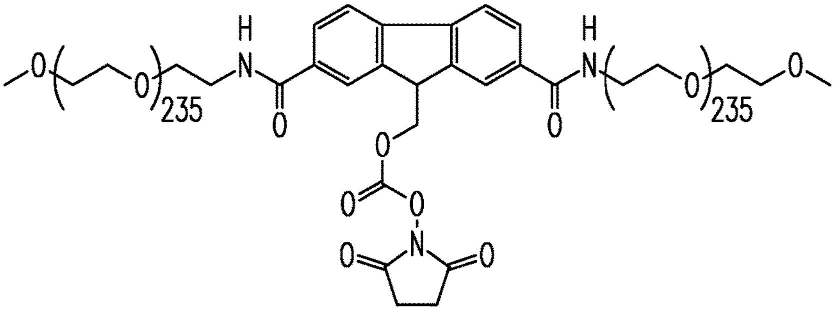
Molecular Weight: 21244.45
FIG.3A
| | |
|---|---|
| PEG amine MW | 21244 |
| IL-2 MW | 15328 |
| | |
| 3 conjugations MW | 79060 |
| 4 conjugations MW | 100304 |
| 5 conjugations MW | 121548 |
FIG.3B
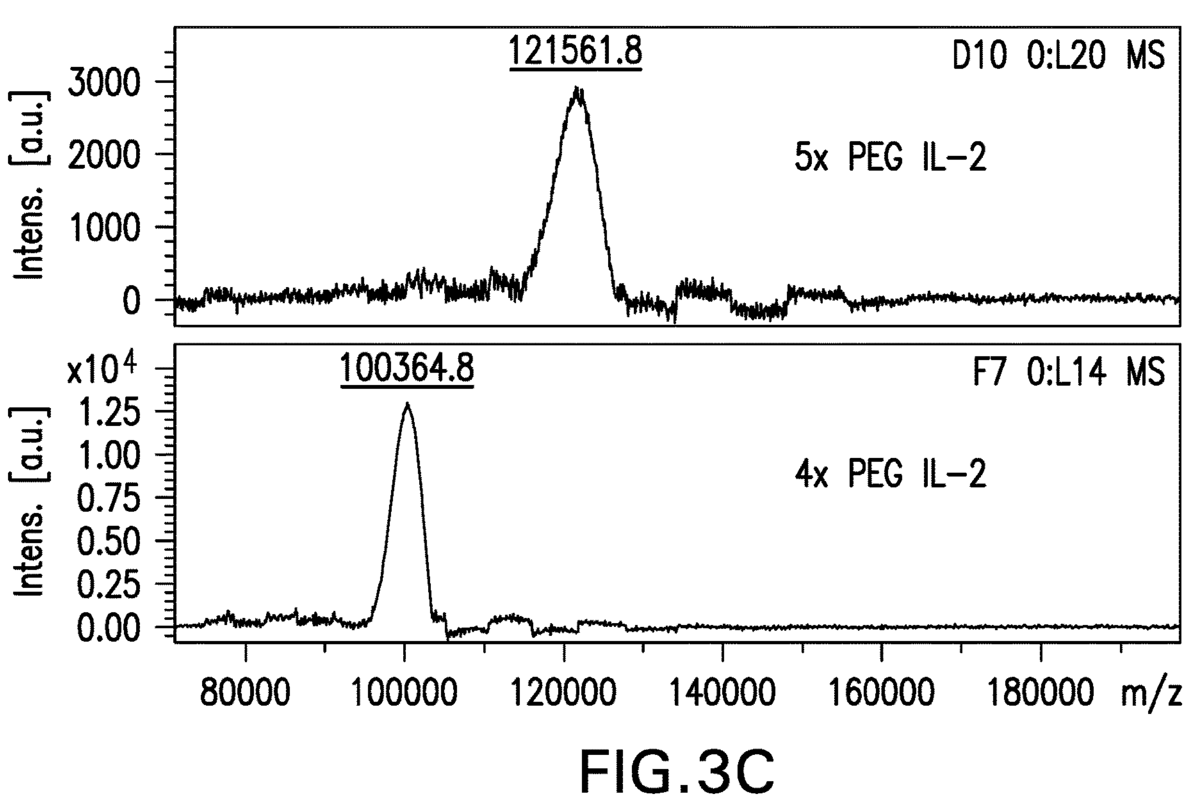
FIG.3C

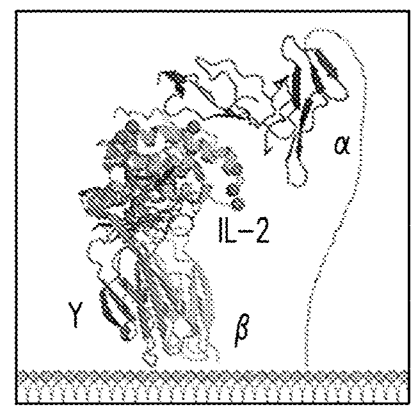

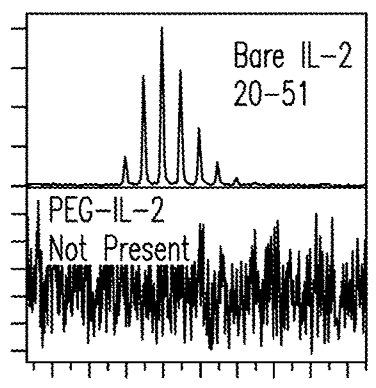

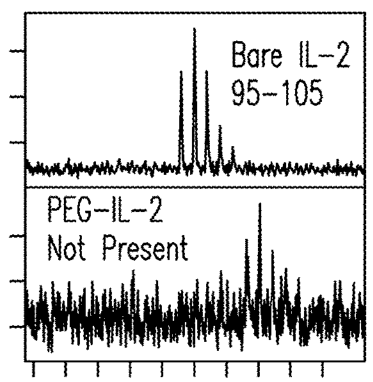

Bare IL-2 Peptide Coverage

```
           10         20         30         40
PTSSSTKKTQ LQLEHLLLDL QMILNGINNY KNPKLTRMLT
           50         60         70         80
FKFYMPKKAT ELKHLQCLEE ELKPLEEVLN LAQSKNFHLR
           90        100        110        120
PRDLISNINV IVLELKGSET TFMCEYADET ATIVEFLNRW
          130        140
ITFSQSIIST LT    88.6%
```

PEG-IL-2 Peptide Coverage

```
           10         20         30         40
PTSSSTKKTQ LQLEHLLLDL QMILNGINNY KNPKLTRMLT
           50         60         70         80
FKFYMPKKAT ELKHLQCLEE ELKPLEEVLN LAQSKNFHLR
           90        100        110        120
PRDLISNINV IVLELKGSET TFMCEYADET ATIVEFLNRW
          130        140
ITFSQSIIST LT    51.5%
```

Sites of PEGylation

```
1                              31 34
PTSSSTKKTQLQLEHLLLDLQMILNGINNYKNPKL
      42  47/48*
TRMLTFKFYMPKKATELKHLQCLEEELKPLEEVLN
                              96
LAQSKNFHLRPRDLISNINVIVLELKGSETTFMCE
                              132
YADETATIVEFLNRWITFSQSIISTLT
```

__ Proposed sites of PEGylation

[ ] Not covered in either construct

*Treated as 1 site-modifying both sites at the same time is sterically hindered.

FIG.4

PROCESSES FOR PREPARING CONJUGATES OF THE IL-2 PROTEIN

This application is a National Stage application of International Patent Application No. PCT/US2021/032662, filed May 17, 2021, which claims the benefit of U.S. Provisional Application No. 63/029,189, filed May 22, 2020, both of which are hereby incorporated by reference in their entirety.

FIELD OF THE INVENTION

Disclosed herein are novel synthetic processes for preparing conjugates of the IL-2 protein. Specifically, processes for preparing the conjugates of the IL-2 protein with water soluble polymers such as poly(ethylene glycol) polymers are described.

CROSS REFERENCE TO RELATED APPLICATIONS

This application claims the benefit of U.S. Provisional Application No. 63/029,189, filed May 22, 2020, hereby incorporated by reference in their entirety.

REFERENCE TO SEQUENCE LISTING SUBMITTED ELECTRONICALLY

The sequence listing of the present application is submitted electronically via EFS-Web as an ASCII formatted sequence listing with a file name 24999PCT-SEQ-LIST.txt, creation date of Apr. 19, 2021, and a size of 1.52 kb. This sequence listing submitted via EFS-Web is part of the specification and is herein incorporated by reference in its entirety.

BACKGROUND OF THE INVENTION

In healthy humans, the immune system can differentiate between healthy cells and cancerous cells. Upon identifying a given cell as cancerous, the immune system typically eliminates it. Thus, when the immune system breaks down or is overwhelmed, cancers can develop resulting from a compromised immune system's inability to differentiate, and then eliminate, cancer cells. In a patient suffering from cancer, administration of an immunomodulatory protein to the patient may help restore the patient's immune system back to normal so that the immune system's ability to eliminate cancer cells returns.

One such immunomodulatory protein used in the treatment of patients suffering from certain cancers is interleukin-2 (IL-2). IL-2 is a naturally occurring cytokine that has activity as both a stimulator of natural killer cells (NK cells) and as an inducer of T-cell proliferation. In unglycosylated form, IL-2 has a molecular weight of about 15,300 Daltons (although IL-2 is found in vivo in variably glycosylated forms).

A commercially available un-glycosylated human recombinant IL-2 product, aldesleukin (available as the PROLEUKIN® brand of des-alanyl-1, serine-125 human interleukin-2 from Prometheus Laboratories Inc., San Diego Calif.), has been approved for administration to patients suffering from metastatic renal cell carcinoma and metastatic melanoma. IL-2 has also been suggested for administration in patients suffering from or infected with hepatitis C virus (HCV), human immunodeficiency virus (HIV), acute myeloid leukemia, non-Hodgkin's lymphoma, cutaneous T-cell lymphoma, juvenile rheumatoid arthritis, atopic dermatitis, breast cancer and bladder cancer.

Even recommended doses of aldesleukin, however, can cause severe side effects, including capillary leak syndrome (CLS) and impaired neutrophil function. Attempts at addressing the toxicity of IL-2 have been tried. In one approach, certain conjugates of IL-2 have been suggested. See, for example, U.S. Pat. Nos. 9,861,705, 4,766,106, 5,206,344, 5,089,261 and 4,902,502.

Currently known processes for preparing IL-2 conjugates with water soluble polymers suffer various drawbacks including requiring high pH values for conjugation reactions and having low yields of the IL-2 conjugates. There remains a need for novel synthetic processes to enable the preparation of IL-2 conjugates with water soluble polymers, or more specifically, with poly(ethylene glycol) ("PEG") polymers, with a high yield and/or at favorable reaction conditions.

BRIEF DESCRIPTION OF THE DRAWINGS

FIG. 1 provides the amino acid sequence of IL-2 following expression and purification and used for conjugation and characterization.

FIG. 3 shows the masses for the PEG moiety, the calculated molecular weights for multiple conjugations to IL-2 and a representative MALDI-TOF mass spectrum following cation exchange purification and ultrafiltration.

FIG. 4 shows peptide coverage maps of IL-2 and PEGylated IL-2 following proteolysis. The sites of modification are modeled onto the sequence and a 3D model of IL-2 with respect to IL-2 receptor α, β & γ.

SUMMARY OF THE INVENTION

Figure 2:
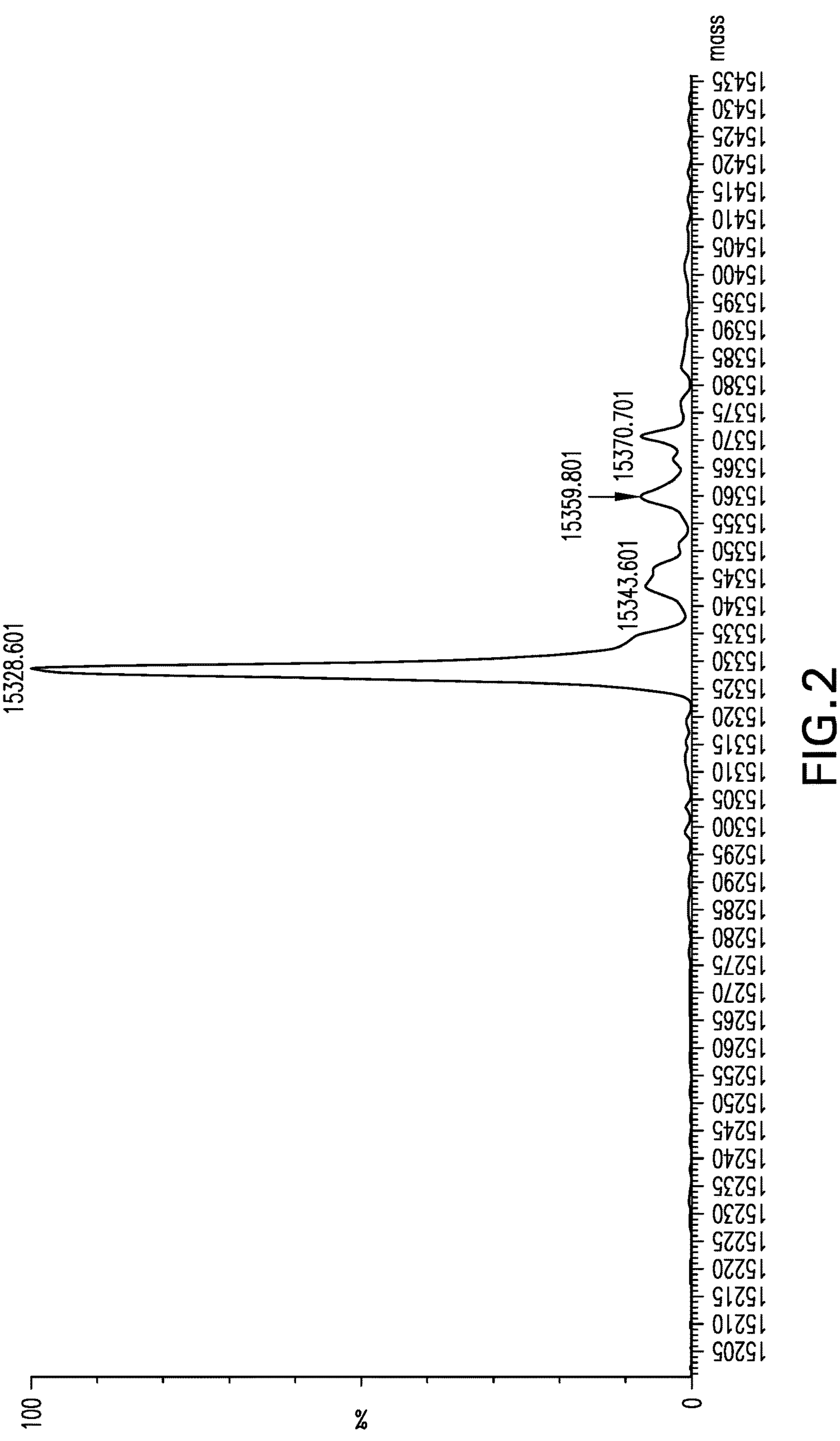
FIG. 2 is a representative deconvoluted mass spectrum showing the intact mass of IL-2 following expression and purification and used for conjugation and characterization.

Accordingly, novel processes for preparing IL-2 conjugates, for example, with one or more water-soluble polymers, are described below.

In one embodiment, a process for preparing a conjugate of an interleukin-2 (IL-2) moiety comprises reacting one or more polymerization agents with the IL-2 moiety to form an IL-2 conjugate, wherein the IL-2 conjugate comprises one or more water-soluble polymers at least one of which is covalently attached to an amino group of the IL-2 moiety; and wherein the conjugation reaction is carried out at a pH of about 8.2 to about 8.8. In another embodiment, the reaction is carried out at a pH of about 8.2 to about 8.6.

In one embodiment, a process for preparing a conjugate of an interleukin-2 (IL-2) moiety comprises reacting one or more polymerization agents with the IL-2 moiety to form an IL-2 conjugate, wherein the polymerization agent is a PEGylating agent; wherein the IL-2 conjugate obtained from the conjugation process comprises one to five poly(ethylene glycol) polymers at least one of which is covalently attached to an amino group of the IL-2 moiety; and wherein the conjugation reaction is carried out at a pH of about 8.2 to about 8.8. In another embodiment, the reaction is carried out at a pH of about 8.2 to about 8.6. In one embodiment, the IL-2 conjugate obtained from the conjugation process comprises five poly(ethylene glycol) polymers at least one of which is covalently attached to an amino group of the IL-2 moiety.

DETAILED DESCRIPTION OF THE INVENTION

It is to be understood that the processes described herein are not limited to the particular water soluble polymers, synthetic techniques, or the IL-2 moieties described below, as these are for illustration only.

The processes described herein enable the preparation of IL-2 conjugates comprising one or more, for example one to five, water soluble polymers covalently attached to the IL-2 moiety and having one or more of the following advantages.

First, the pH value of the conjugation reaction is lowered to about 8.2 to about 8.8, or more specifically, about 8.2 to about 8.6, or more specifically, about 8.4 to about 8.5, or even more specifically, about 8.4.

Second, the polymerization agent, for example, a PEGylating agent, is added to the IL-2 moiety in a water solution instead of an HCl solution.

Third, a high purity PEGylating agent is used in the conjugation reaction. In one embodiment, the purity of the PEGylating agent is greater than about 90%, or more specifically, greater than about 93%, or more specifically, greater than about 94%, or even more specifically, greater than about 95%. In one embodiment, the purity is determined by liquid chromatography area percent. In one embodiment, the high purity PEGylating agent can be obtained by performing a second precipitation on PEG fluorene alcohol prior to NHS ester activation.

One or more of the above advantages contribute to a good overall yield of the IL-2 conjugate. In one embodiment, the overall yield is greater than about 20%, or more specifically, greater than about 23%, or more specifically, greater than about 25%, or even more specifically, greater than about 28%. In one embodiment, the overall yield is about 20% to about 25%.

In one embodiment, a process for preparing a conjugate of an interleukin-2 (IL-2) moiety comprises:

- adding one or more polymerization agents to react with the IL-2 moiety to form an IL-2 conjugate, wherein the IL-2 conjugate comprises one or more water-soluble polymers at least one of which is covalently attached to an amino group of the IL-2 moiety;
- wherein the conjugation reaction is carried out at a pH of about 8.2 to about 8.8.

In one embodiment of the above process, the conjugation reaction is carried out at a pH of about 8.2 to about 8.6.

In one embodiment of the above process, the conjugation reaction is carried out at a pH of about 8.4 to about 8.5.

In one embodiment of the above process, the conjugation reaction is carried out at a pH of about 8.4.

In one embodiment of the above process, the polymerization agents are added to the IL-2 moiety in a water solution. In one embodiment, the polymerization agents are PEGylating agents.

In one embodiment of the above process, the polymerization agent has a purity of greater than about 90%. In one embodiment, the purity is determined by liquid chromatography area percent. In one embodiment, the polymerization agent is PEG fluorene NHS ester. In one embodiment, the PEG fluorene NHS ester has a purity of greater than about 90% as determined by liquid chromatography area percent.

In one embodiment of the above process, the polymerization agent has a purity of greater than about 93%. In one embodiment, the purity is determined by liquid chromatography area percent. In one embodiment, the polymerization agent is PEG fluorene NHS ester. In one embodiment, the PEG fluorene NHS ester has a purity of greater than about 93% as determined by liquid chromatography area percent.

In one embodiment of the above process, the polymerization agent has a purity of greater than about 95%. In one embodiment, the purity is determined by liquid chromatography area percent. In one embodiment, the polymerization agent is PEG fluorene NHS ester. In one embodiment, the PEG fluorene NHS ester has a purity of greater than about 95% as determined by liquid chromatography area percent.

In one embodiment of the above process, the polymerization agent is a PEG fluorene NHS ester.

In one embodiment of the above process, the IL-2 conjugate comprises one to five water-soluble polymers, and wherein each of the water-soluble polymers in the conjugate is covalently attached to an amino group of the IL-2 moiety.

In one embodiment of the above process, the IL-2 conjugate comprises five water-soluble polymers, and wherein each of the water-soluble polymers in the conjugate is covalently attached to an amino group of the IL-2 moiety.

In one embodiment of the above process, all water-soluble polymers in the IL-2 conjugate is covalently attached to an amino group of the IL-2 moiety via a releasable linkage.

In one embodiment of the above process, the releasable linkage is a covalent linkage between a water-soluble polymer and an amino group of a lysine of the IL-2 moiety.

In one embodiment of the above process, the water-soluble polymer is a poly(ethylene glycol) polymer.

In one embodiment of the above process, the polymerization agent is a PEGylating agent, and wherein the IL-2 conjugate obtained from the conjugation process comprises one to five poly(ethylene glycol) polymers at least one of which is covalently attached to an amino group of the IL-2 moiety.

In one embodiment of the above process, the IL-2 conjugate obtained from the conjugation process comprises five poly(ethylene glycol) polymers at least one of which is covalently attached to an amino group of the IL-2 moiety.

In one embodiment of the above process, the PEGylating agent comprises one or more branched poly(ethylene glycol) polymers.

In one embodiment of the above process, the PEGylating agent is a PEG fluorene NHS ester.

In one embodiment of the above process, the PEGylating agent is a PEG fluorene NHS ester having a weight-average molecular weight of about 5,000 to about 30,000.

In one embodiment of the above process, the PEGylating agent is a PEG fluorene NHS ester having a weight-average molecular weight of about 10,000 to about 30,000.

In one embodiment of the above process, the PEGylating agent is a PEG fluorene NHS ester having a weight-average molecular weight of about 15,000 to about 25,000.

In one embodiment of the above process, the PEGylating agent is a PEG fluorene NHS ester having a weight-average molecular weight of about 20,000 to about 25,000.

In one embodiment of the above process, the PEGylating agent is a PEG fluorene NHS ester having a weight-average molecular weight of about 20,000 to about 22,000.

In one embodiment of the above process, the PEGylating agent comprises one or more branched poly(ethylene glycol) polymers.

In one embodiment of the above process, the PEGylating agent comprises two branched poly(ethylene glycol) polymers.

In one embodiment of the above process, the PEGylating agent is a PEG fluorene NHS ester having the following formula:

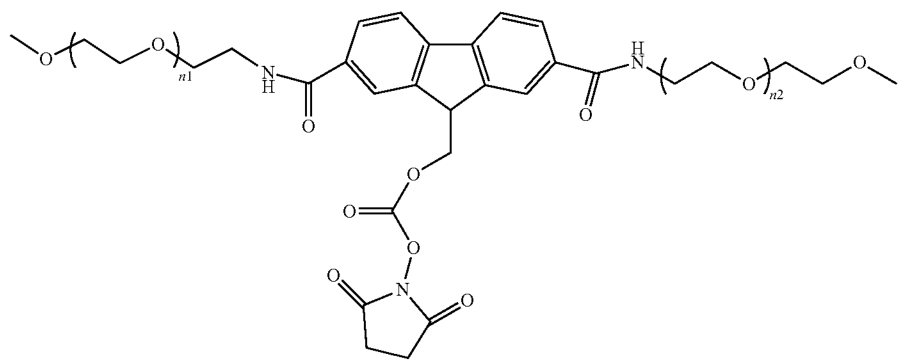

wherein each of n1 and n2 is independently selected from 150-300.

In one embodiment of the above process, each of n1 and n2 is independently selected from 200-250.

In one embodiment of the above process, the PEGylating agent is a PEG fluorene NHS ester having the following formula:

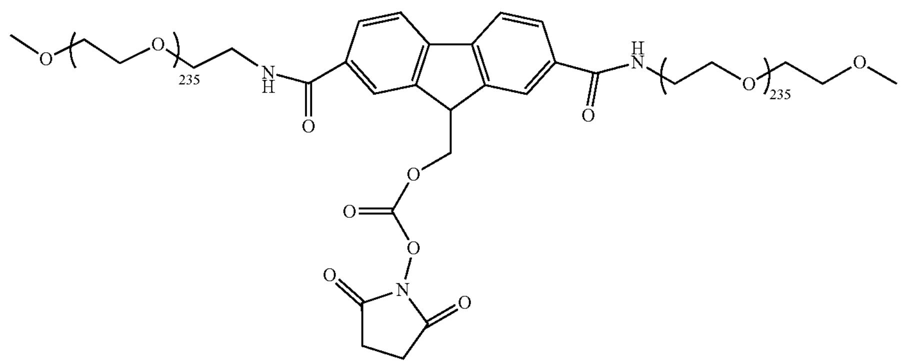

In one embodiment of the above process, the PEG fluorene NHS ester has a purity of greater than about 90% as determined by liquid chromatography area percent.

In one embodiment of the above process, the PEG fluorene NHS ester has a purity of greater than about 93% as determined by liquid chromatography area percent.

In one embodiment of the above process, the PEG fluorene NHS ester has a purity of greater than about 95% as determined by liquid chromatography area percent.

In one embodiment of the above process, the PEGylating agent is a solution in water.

In one embodiment of the above process, the overall yield of the IL-2 conjugate is greater than 20%. In one embodiment of the above process, the overall yield of the IL-2 conjugate is greater than 23%. In one embodiment of the above process, the overall yield of the IL-2 conjugate is greater than 25%. In one embodiment of the above process, the overall yield of the IL-2 conjugate is greater than 28%. In one embodiment of the above process, the overall yield of the IL-2 conjugate is greater than 30%.

In one embodiment of the above process, the overall yield of the IL-2 conjugate is about 20-25%.

In one embodiment of the above process, the degree of PEGylation can be determined by MALDI analysis. The sites of PEGylation can be determined by digestion analysis.

In one embodiment of the above process, the PEGylating agent is reacted with the IL-2 moiety to form a conjugate comprising five poly(ethylene glycol) polymers, wherein at least one of the poly(ethylene glycol) polymers is covalently attached to the IL-2 moiety via a releasable linkage to an amino group within the IL-2 moiety.

In one embodiment of the above process, each of the five poly(ethylene glycol) polymers is covalently attached to the IL-2 moiety via a releasable linkage to an amino group of a lysine of the IL-2 moiety.

In one embodiment, a poly(ethylene glycol) polymer is covalently attached to the lysine at position 31 of the IL-2 moiety. In one embodiment, a poly(ethylene glycol) polymer is covalently attached to the lysine at position 34 of the IL-2 moiety. In one embodiment, a poly(ethylene glycol) polymer is covalently attached to the lysine at position 42 of the IL-2 moiety. In one embodiment, a poly(ethylene glycol) polymer is covalently attached to the lysine at position 47 of the IL-2 moiety. In one embodiment, a poly(ethylene glycol) polymer is covalently attached to the lysine at position 48 of the IL-2 moiety. In one embodiment, a poly(ethylene glycol) polymer is covalently attached to the lysine at position 96 of the IL-2 moiety. In one embodiment, the IL-2 moiety has SEQ ID No. 1.

In one embodiment, poly(ethylene glycol) polymers are covalently attached to the lysines at positions 31, 34, 42 and 47 of the IL-2 moiety. In one embodiment, poly(ethylene glycol) polymers are covalently attached to the lysines at positions 31, 34, 42 and 48 of the IL-2 moiety. In one embodiment, the IL-2 moiety has SEQ ID No. 1.

In one embodiment, poly(ethylene glycol) polymers are covalently attached to the lysine at positions 31, 34, 42, 47 and 96 of the IL-2 moiety. In one embodiment, poly(ethylene glycol) polymers are covalently attached to the lysine at positions 31, 34, 42, 48 and 96 of the IL-2 moiety. In one embodiment, the IL-2 moiety has SEQ ID No. 1.

In one embodiment, the IL-2 conjugate with five poly (ethylene glycols) has a desirable half-life. In another embodiment, the IL-2 conjugate with five poly(ethylene glycols) has a high yield. In another embodiment, the IL-2 conjugate with five poly(ethylene glycols) has a high purity. In another embodiment, the IL-2 conjugate with five poly (ethylene glycols) has a desirable activity.

In one embodiment of the above process, the purity of the isolated 5× PEGylated IL-2 conjugate is greater than 70%, or more specifically, greater than 75%, or more specifically, greater than 80%, or more specifically, greater than 85%, or more specifically, greater than 90%, or more specifically, greater than 93%, or even more specifically, greater than 95%. The major impurities are PEGylated IL-2 conjugates with a different number of conjugated water soluble PEGs.

In one embodiment of the above process, each branched poly(ethylene glycol) polymer has a weight-average molecular weight of about 1,000 Daltons to about 30,000 Daltons.

In one embodiment of the above process, each branched poly(ethylene glycol) polymer has a weight-average molecular weight of about 1,000 Daltons to about 25,000 Daltons.

In one embodiment of the above process, each branched poly(ethylene glycol) polymer has a weight-average molecular weight of about 1,500 Daltons to about 20,000 Daltons.

In one embodiment of the above process, each branched poly(ethylene glycol) polymer has a weight-average molecular weight of about 1,500 Daltons to about 5,000 Daltons.

In one embodiment of the above process, each branched poly(ethylene glycol) polymer has a weight-average molecular weight of about 1,500 Daltons to about 3,000 Daltons.

In one embodiment of the above process, each branched poly(ethylene glycol) polymer has a weight-average molecular weight of about 2,000 Daltons to about 2,500 Daltons.

In one embodiment of the above process, each branched poly(ethylene glycol) polymer has a weight-average molecular weight of about 2,000 Daltons to about 2,300 Daltons.

In one embodiment of the above process, each branched poly(ethylene glycol) polymer has a weight-average molecular weight of about 2,100 Daltons to about 2,200 Daltons.

In one embodiment of the above process, each branched poly(ethylene glycol) comprises two poly(ethylene glycol) chains.

As used herein, singular forms "a," "an," and "the" include plural referents unless the context clearly dictates otherwise. Thus, for example, reference to "a polymer" includes a single polymer as well as two or more of the same or different polymers.

In describing and claiming one or more embodiments, the following terminology will be used in accordance with the definitions described below.

As used herein, "PEG," "polyethylene glycol" and "poly (ethylene glycol)" are interchangeable and encompass any nonpeptidic water-soluble poly(ethylene oxide). Typically, PEGs for use in accordance with the invention comprise the following structure "$—(OCH_2CH_2)_n—$" where (n) is 10 to 2000, or more specifically, 50 to 1000, or more specifically, 150 to 500, or more specifically, 150 to 300, or even more specifically, 200 to 250. As used herein, PEG also includes "$—CH_2CH_2—O—(CH_2CH_2O)_n—CH_2CH_2—$" and "$—(OCH_2CH_2)_nO—$," depending upon whether or not the terminal oxygens have been displaced, e.g., during a synthetic transformation.

In one embodiment, the term "PEG" includes structures having various terminal or "end capping" groups.

In one embodiment, the term "PEG" also means a polymer that contains a majority, for example, greater than 50%, or more specifically, greater than 60%, or more specifically, greater than 70%, or even more specifically, greater than 80%, of $—OCH_2CH_2—$ repeating subunits. With respect to specific forms, the PEG can take any number of a variety of molecular weights, as well as structures or geometries such as "branched," "linear," "forked," "multifunctional," as described in more detail below. In one embodiment, the PEG has a branched structure.

The terms "end-capped" and "terminally capped" are interchangeably used herein to refer to a terminal or end-point of a polymer having an end-capping moiety. In one embodiment, the end-capping moiety comprises a hydroxy or $C_{1-20}$ alkoxy group, or more specifically, a $C_{1-10}$ alkoxy group, or more specifically, a $C_{1-5}$ alkoxy group, or even more specifically, a $C_{1-3}$ alkoxy group. Thus, examples of end-capping moieties include alkoxy (e.g., methoxy, ethoxy and propoxy). The end-capping moiety may include one or more atoms of the terminal monomer in the polymer, for example, the end-capping moiety "methoxy" in $CH_3O(CH_2CH_2O)_n—$ and $CH_3(OCH_2CH_2)_n—$. In addition, saturated, unsaturated, substituted and unsubstituted forms of each of the foregoing are envisioned.

Moreover, the end-capping group can also be a silane. The end-capping group can comprise a detectable label. When the polymer has an end-capping group comprising a detectable label, the amount or location of the polymer and/or the moiety (e.g., active agent) to which the polymer is coupled can be determined by using a suitable detector. Such labels include, but are not limited to, fluorescers, chemiluminescers, moieties used in enzyme labeling, colorimetric (e.g., dyes), metal ions, and radioactive moieties. Suitable detectors include, but are not limited to, photometers, films, and spectrometers.

The end-capping group can also comprise a phospholipid. When the polymer has an end-capping group comprising a phospholipid, unique properties are imparted to the polymer and the resulting conjugate. Exemplary phospholipids include, but are not limited to, those selected from the class of phospholipids called phosphatidylcholines. Specific phospholipids include, but are not limited to, those selected from the group consisting of dilauroylphosphatidylcholine, dioleylphosphatidylcholine, dipalmitoylphosphatidylcholine, di steroylphosphatidylcholine, behenoylphosphatidylcholine, arachidoylphosphatidylcholine, and lecithin.

The end-capping group may also include a targeting moiety, such that the polymer as well as anything, e.g., an IL-2 moiety, attached thereto can preferentially localize in an area of interest.

"Non-naturally occurring" with respect to a polymer as described herein, means a polymer that in its entirety is not found in nature. A non-naturally occurring polymer may, however, contain one or more monomers or segments of monomers that are naturally occurring, so long as the overall polymer structure is not found in nature.

The term "water soluble" as in a "water-soluble polymer" is any polymer that is soluble in water at room temperature.

In one embodiment, a water-soluble polymer will transmit at least about 75%, or more specifically at least about 95%, of light transmitted by the same solution after filtering. In one embodiment, a water-soluble polymer is at least about 50% by weight soluble in water, or more specifically, at least about 60% by weight soluble in water, or more specifically, at least about 70% by weight soluble in water, or more specifically, at least about 80% by weight soluble in water, or even more specifically, at least about 90% by weight soluble in water. In one embodiment, the water-soluble polymer is about 95% by weight soluble in water or completely soluble in water.

Molecular weight in the context of a water-soluble polymer, such as a PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Mass spectrometry techniques, including matrix-assisted laser desorption/ionization and eletrospray-ionization mass spectrometry, can also be used for molecular weight determination. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers disclosed herein are typically polydisperse (i.e., number average molecular weight and weight average molecular weight of the polymers are not equal), possessing low polydispersity values of less than about 1.2, or more specifically, less than about 1.15, or more specifically, less than about 1.10, or more specifically, less than about 1.05, or even more specifically, less than about 1.03.

The terms "active," "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" and "linker" are used herein to refer to a bond or an atom or a collection of atoms optionally used to link interconnecting moieties such as a terminus of a polymer segment and an IL-2 moiety or an electrophile or nucleophile of an IL-2 moiety. The spacer moiety may be hydrolytically stable or may include a physiologically hydrolyzable or enzymatically degradable linkage. Unless the context clearly dictates otherwise, a spacer moiety optionally exists between any two elements of a compound (e.g., the provided conjugates comprising a residue of IL-2 moiety and water-soluble polymer can be attached directly or indirectly through a spacer or linker moiety).

"Alkyl" refers to a hydrocarbon chain, typically ranging from about 1 to 12 atoms in length. Such hydrocarbon chains may be branched or straight chains. Exemplary alkyl groups include methyl, ethyl, propyl, butyl, pentyl, 1-methylbutyl, 1-ethylpropyl, and 3-methylpentyl. As used herein, "alkyl" includes cycloalkyl as well as cycloalkylene-containing alkyl.

The term "substituted" as in, for example, "substituted alkyl," refers to a moiety (e.g., an alkyl group) substituted with one or more noninterfering substituents, such as, but are not limited to, $C_{3-8}$ cycloalkyl, for example, cyclopropyl, and cyclobutyl; halo, for example, fluoro, chloro, bromo, and iodo; cyano; alkoxy; phenyl; and substituted phenyl.

"Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings.

"Electrophile" and "electrophilic group" refer to an ion or atom or collection of atoms, which may be ionic, having an electrophilic center, for example, a center that is electron seeking, capable of reacting with a nucleophile.

"Nucleophile" and "nucleophilic group" refers to an ion or atom or collection of atoms that may be ionic having a nucleophilic center, for example, a center that is seeking an electrophilic center or with an electrophile.

A "physiologically cleavable" or "hydrolyzable" or "degradable" bond is a bond that reacts with water (i.e., is hydrolyzed) under physiological conditions. The tendency of a bond to hydrolyze in water not only depends on the general type of the linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, which is substantially stable in water, that is to say, does not undergo hydrolysis under physiological conditions to any appreciable extent over an extended period of time. Examples of hydrolytically stable linkages include, but are not limited to, carbon-carbon bonds (e.g., in aliphatic chains), ethers, amides, and urethanes. Generally, a hydrolytically stable linkage is one that exhibits a rate of hydrolysis of less than about 1-2% per day under physiological conditions. Hydrolysis rates of representative chemical bonds can be found in standard chemistry textbooks.

"Multi-functional" means a polymer having three or more functional groups contained therein, where the functional groups may be the same or different. Multi-functional polymeric reagents typically contain from about 3-100 functional groups, or from 3-50 functional groups, or from 3-25 functional groups, or from 3-15 functional groups, or from 3 to 10 functional groups, or contain 3, 4, 5, 6, 7, 8, 9 or 10 functional groups within the polymer backbone.

The term "IL-2 moiety" refers to IL-2, or a derivative thereof, having human IL-2 activity. The IL-2 moiety disclosed herein has at least one electrophilic group or nucleophilic group suitable for reaction with a polymeric reagent. In addition, the term "IL-2 moiety" encompasses both the IL-2 moiety prior to conjugation as well as the IL-2 moiety residue following conjugation. As described in more detail below, one of ordinary skill in the art can determine whether any given moiety has IL-2 activity. Proteins comprising an amino acid sequence corresponding to SEQ ID NO: 1 is an IL-2 moiety, as well as any protein or polypeptide substantially homologous thereto, for example, having 80 percent homology, or 85 percent homology, or 90 percent homology, or 95 percent homology, or 98 percent homology.

As used herein, the term "IL-2 moiety" also includes a modified IL-2 protein, for example, by site directed mutagenesis or accidentally through mutations. These terms also include analogs having from 1 to 6 additional glycosylation sites, analogs having at least one additional amino acid at the carboxy terminal end of the protein wherein the additional amino acid(s) includes at least one glycosylation site, and analogs having an amino acid sequence which includes at least one glycosylation site. The term includes both natural and recombinantly produced moieties.

The term "substantially homologous" means that a particular subject sequence, for example, a mutant sequence, varies from a reference sequence by one or more substitutions, deletions, or additions, the net effect of which does not result in an adverse functional dissimilarity between the reference and subject sequences. In one embodiment, sequences having greater than 80 percent, or more specifically, greater than 85 percent, or more specifically, greater than 90 percent, or more specifically, greater than 95 percent homology, or more specifically, greater than 98 percent equivalent biological activity (although not necessarily equivalent strength of biological activity), and equivalent expression characteristics are considered substantially homologous. For purposes of determining homology, truncation of the mature sequence should be disregarded. Exemplary IL-2 moieties for use herein include those sequences that are substantially homologous to SEQ ID NO: 1.

The term "fragment" means any protein or polypeptide having the amino acid sequence of a portion or fragment of an IL-2 moiety, and which has the biological activity of IL-2. Fragments include proteins or polypeptides produced by proteolytic degradation of an IL-2 moiety as well as proteins or polypeptides produced by chemical synthesis by methods routine in the art.

"Optional" or "optionally" means that the subsequently described circumstance may or may not occur, so that the description includes instances where the circumstance occurs and instances where it does not.

"Substantially" means satisfying one or more of the following: greater than 50%, greater than 60%, greater than 75%, greater than 80%, greater than 90%, or greater than 95%, or greater than 98%, of a condition.

A conjugate of an IL-2 protein with one or more water-soluble polymers comprises a residue of the IL-2 moiety covalently attached (either directly or through a spacer moiety) to the one or more water-soluble polymers.

The IL-2 Moiety

As previously stated, the conjugate generically comprises a residue of an IL-2 moiety covalently attached, either directly or through a spacer moiety, to a water-soluble polymer. As used herein, the term "IL-2 moiety" shall refer to the IL-2 moiety prior to conjugation as well as to the IL-2 moiety following attachment to a nonpeptidic, water-soluble polymer. In one embodiment, when the original IL-2 moiety is attached to a nonpeptidic, water-soluble polymer, the IL-2 moiety is slightly altered due to the presence of one or more covalent bonds associated with linkage to the polymer(s). Often, this slightly altered form of the IL-2 moiety attached to another molecule is referred to a "residue" of the IL-2 moiety.

The IL-2 moiety can be derived from non-recombinant methods and from recombinant methods and the invention is not limited in this regard. In addition, the IL-2 moiety can be derived from human sources, animal sources, and plant sources.

The IL-2 moiety can be derived non-recombinantly. For example, it is possible to isolate IL-2 from biological systems and otherwise obtain IL-2 from cultured media. See, for example, the procedures described in U.S. Pat. No. 4,401,756 and in Pauly et al. (1984) *J. Immunol Methods* 75(1):73-84.

The IL-2 moiety can be derived from recombinant methods. See, for example, U.S. Pat. No. 5,614,185, the disclosure and the Experimental provided herein.

Any IL-2 moiety obtained non-recombinant and recombinant approaches can be used as an IL-2 moiety in preparing the conjugates described herein.

The IL-2 moiety can be expressed in bacterial [e.g., *E. cola*], mammalian, yeast [e.g., *Pichia pastoris*], and plant expression systems. The expression can occur via exogenous expression (when the host cell naturally contains the desired genetic coding) or via endogenous expression.

Although recombinant-based methods for preparing proteins can differ, recombinant methods typically involve constructing the nucleic acid encoding the desired polypeptide or fragment, cloning the nucleic acid into an expression vector, transforming a host cell (e.g., plant, bacteria, yeast, transgenic animal cell, or mammalian cell such as Chinese hamster ovary cell or baby hamster kidney cell), and expressing the nucleic acid to produce the desired polypeptide or fragment. Methods for producing and expressing recombinant polypeptides in vitro and in prokaryotic and eukaryotic host cells are known to those of ordinary skill in the art.

To facilitate identification and purification of the recombinant polypeptide, nucleic acid sequences that encode for an epitope tag or other affinity binding sequence can be inserted or added in-frame with the coding sequence, thereby producing a fusion protein comprised of the desired polypeptide and a polypeptide suited for binding. Fusion proteins can be identified and purified by first miming a mixture containing the fusion protein through an affinity column bearing binding moieties (e.g., antibodies) directed against the epitope tag or other binding sequence in the fusion proteins, thereby binding the fusion protein within the column. Thereafter, the fusion protein can be recovered by washing the column with the appropriate solution (e.g., acid) to release the bound fusion protein. The recombinant polypeptide can also be purified by lysing the host cells, separating the polypeptide, e.g., by ion-exchange chromatography, affinity binding approaches, hydrophobic interaction approaches, and thereafter identify by MALDI or western blot, and collecting the polypeptide. These and other methods for identifying and purifying recombinant polypeptides are known to those of ordinary skill in the art. In one or more embodiments of the invention, however, the IL-2 moiety is not in the form of a fusion protein.

Depending on the system used to express proteins having IL-2 activity, the IL-2 moiety can be un-glycosylated or glycosylated and either may be used. That is, the IL-2 moiety can be un-glycosylated or the IL-2 moiety can be glycosylated. In one or more embodiments of the invention, the IL-2 moiety is unglycosylated.

The IL-2 moiety can be modified to include and/or substitute one or more amino acid residues such as, for example, lysine, cysteine and/or arginine, in order to provide facile attachment of the polymer to an atom within the side chain of the amino acid. An example of substitution of an IL-2 moiety is described in U.S. Pat. No. 5,206,344. In addition, the IL-2 moiety can be modified to include a non-naturally occurring amino acid residue. Techniques for adding amino acid residues and non-naturally occurring amino acid residues are well known to those of ordinary skill in the art. Reference is made to J. March, Advanced Organic Chemistry: Reactions Mechanisms and Structure, 4th Ed. (New York: Wiley-Interscience, 1992).

In addition, the IL-2 moiety can be modified to include attachment of a functional group (other than through addition of a functional group-containing amino acid residue). For example, the IL-2 moiety can be modified to include a thiol group. In addition, the IL-2 moiety can be modified to include an N-terminal alpha carbon. In addition, the IL-2 moiety can be modified to include one or more carbohydrate moieties. In addition, the IL-2 moiety can be modified to include an aldehyde group. In addition, the IL-2 moiety can be modified to include a ketone group. In some embodiments of the invention, it is preferred that the IL-2 moiety is not modified to include one or more of a thiol group, an N-terminal alpha carbon, carbohydrate, aldehyde group and ketone group.

Exemplary IL-2 moieties are described in the literature and in, for example, U.S. Pat. Nos. 5,116,943, 5,153,310, 5,635,597, 7,101,965 and 7,567,215 and U.S. Patent Application Publication Nos. 2010/0036097 and 2004/0175337. Preferred IL-2 moiety has an amino acid sequence of SEQ ID NO: 1, and sequences substantially homologous thereto. In one embodiment, an IL-2 moiety has the amino acid sequence corresponding to SEQ ID NO: 1.

In one embodiment, the IL-2 moiety is in a "monomer" form, wherein a single expression of the corresponding peptide is organized into a discrete unit. In another embodiment, the IL-2 moiety is in the form of a "dimer" (e.g., a dimer of recombinant IL-2) wherein two monomer forms of the protein are associated (e.g., by disulfide bonding) to each other. For example, in the context of a dimer of recombinant human IL-2, the dimer may be in the form of two monomers associated to each other by a disulfide bond formed from each monomer's Cys125 residue.

In addition, precursor forms IL-2 can be used as the IL-2 moiety. An exemplary precursor form of IL-2 has the sequence of SEQ ID NO: 1.

Truncated versions, hybrid variants, and peptide mimetics of any of the foregoing sequences can also serve as the IL-2 moiety. Biologically active fragments, deletion variants, substitution variants or addition variants of any of the foregoing that maintain at least 25%, or more specifically, at least 30%, or more specifically, at least 35%, or more specifically, at least 40%, or more specifically, at least 45%, or even more specifically, at least 50%, of IL-2 activity can also serve as an IL-2 moiety.

For any given peptide or protein moiety, it is possible to determine whether that moiety has IL-2 activity. Various methods for determining the in vitro IL-2 activity are described in the art. An exemplary approach is the CTTL-2 cell proliferation assay described in the experimental below. An exemplary approach is described in Moreau et al. (1995) *Mol. Immunol.* 32:1047-1056). Briefly, in a non-specific binding assay, a proposed IL-2 moiety is allowed to preincubate for one hour at 4° C. in the presence of a cell line bearing a receptor of IL-2. Thereafter, $^{125}$I-labelled IL-2 is allowed to incubate in the system for three hours at 4° C. Data is expressed as % inhibitory capacity of the proposed IL-2 moiety activity versus wild-type IL-2. Other methodologies known in the art can also be used to assess IL-2 function, including electrometry, spectrophotometry, chromatography, and radiometric methodologies.

Water-Soluble Polymers

In one embodiment, an IL-2 conjugate comprises an IL-2 moiety attached to a water-soluble polymer. The water-soluble polymer is nonpeptidic, nontoxic, non-naturally occurring and biocompatible. With respect to biocompatibility, a substance is considered biocompatible if the beneficial effects associated with use of the substance alone or with another substance (e.g., an active agent such as an IL-2 moiety) in connection with living tissues (e.g., administration to a patient) outweighs any deleterious effects as evaluated by a clinician, e.g., a physician. With respect to non-immunogenicity, a substance is considered non-immunogenic if the intended use of the substance in vivo does not produce an undesired immune response (e.g., the formation of antibodies) or, if an immune response is produced, that such a response is not deemed clinically significant or important as evaluated by a clinician. In one embodiment, the nonpeptidic water-soluble polymer is biocompatible and non-immunogenic. Further, the polymer is typically characterized as having from 2 to about 300 termini. Examples of such polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines ("POZ") (which are described in WO 2008/106186), poly(N-acryloylmorpholine), and combinations of any of the foregoing.

The water-soluble polymer is not limited to a particular structure and can be linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the water-soluble polymer can be organized in any number of different repeat patterns and can be selected from the group consisting of homopolymer, alternating copolymer, random copolymer, block copolymer, alternating tripolymer, random tripolymer, and block tripolymer.

Polyethylene glycol (PEG) has been widely used in biomaterials, biotechnology and medicine partly because PEG is a biocompatible, nontoxic, nonimmunogenic and water-soluble polymer (Zhao and Harris, ACS Symposium Series 680: 458-72, 1997). In the area of drug delivery, PEG derivatives have been widely used in covalent attachment (i.e., "PEGylation") to proteins to reduce immunogenicity, proteolysis and kidney clearance and to enhance solubility (Zalipsky, Adv. Drug Del. Rev. 16:157-82, 1995). Similarly, PEG has been attached to low molecular weight, relatively hydrophobic drugs to enhance solubility, reduce toxicity and alter biodistribution. Typically, PEGylated drugs are injected as solutions.

In one embodiment, the polyethylene glycol has a molecular weight ranging from about 1 kilodalton (kD) to about 5000 kD, or more specifically, from about 1 kD to about 2000 kD, or more specifically, from about 1 kD to about 1000 kD, or more specifically, from about 5 kD to about 500 kD, or more specifically, from about 10 kD to about 250 kD. Covalent attachment of the PEG to a protein drug (known as "PEGylation") may be accomplished by known chemical synthesis techniques. For example, in one aspect of the present invention, the PEGylation of protein may be accomplished by reacting NHS-activated PEG with the protein under suitable reaction conditions.

While numerous reactions have been described for PEGylation, those that are most generally applicable confer directionality, utilize mild reaction conditions, and do not necessitate extensive downstream processing to remove undesirable catalysts or bi-products. Suitable PEGs include methoxyPEGs (mPEGs) where there are one or more terminal methoxy groups. Activation of the hydroxyl group at the end of the polymer opposite to the terminal methoxy group is generally necessary to accomplish efficient protein PEGylation, with the aim being to make the derivatized PEG more susceptible to nucleophilic attack. The attacking nucleophile is usually the epsilon-amino group of a lysyl residue, but other amines can also react (e.g. the N-terminal alpha-amine or the ring amines of histidine) if local conditions are favorable. A more directed attachment is possible in proteins containing a single lysine or cysteine. The latter residue can be targeted by PEG-maleimide for thiol-specific modification.

Examples of suitable polymeric molecules include polymeric molecules selected from the group comprising polyalkylene oxides (PAO), such as polyalkylene glycols (PAG), including polyethylene glycols (PEG), methoxypolyethylene glycols (mPEG) and polypropylene glycols, PEG-glycidyl ethers (Epox-PEG), PEG-oxycarbonylimidazole (CPI-PEG) branched polyethelene glycols (PEGs), polyvinyl alcohol) PVA), polycarboxylates, polyvinylpyrrolidone, poly-D, L-amino acids, polyethylene-co-maleic acid anhydride, polystyrene-co-malic acid arhydride, dextrans including carboxymethyl-dextrans, heparin, homologous albumin, celluloses, including methylcellulose, carboxymethylcellulose, ethylcellulosia, hydroxyethylcellulose carboxyethylcellulose and hydroxypropylcellulose, hydrolysates of chitosan, starches such as hydroxyethyl-starches and hydroxy propyl-starches, glycogen, agaroses and derivatives thereof, guar gum, pullulan, inulin, xanthan gum, carrageenan, pectin, alginic acid hydrolysates and bio-polymers.

When used as the polymer, PEGs typically comprise a number of ($OCH_2CH_2$) monomers (or ($CH_2CH_2O$) monomers, depending on how the PEG is defined). As used herein, the number of repeating units is identified by the subscript "n" in "$(OCH_2CH_2)_n$." The value of "n" typically falls within one or more of the following ranges: from 2 to about 3500, from about 100 to about 2000, from about 150 to about 1500, from about 150 to about 1000, from about 200 to about 500, from about 220 to about 400, from about 225 to about 300, from about 230 to about 260, from about 235 to about 250, and about 235. For any given polymer in which the molecular weight is known, it is possible to determine the number of repeating units (i.e., "n") by dividing the total weight-average molecular weight of the polymer by the molecular weight of the repeating monomer.

In one embodiment, the polymer disclosed herein is an end-capped polymer, that is, a polymer having at least one terminus capped with a relatively inert group, such as a lower $C_{1-6}$ alkoxy group or a hydroxyl group. When the polymer is a PEG, for example, a methoxy-PEG (commonly referred to as mPEG) can be used, which is a linear form of PEG wherein one terminus of the polymer is a methoxy ($—OCH_3$) group, while the other terminus is a hydroxyl or other functional group that can be optionally chemically modified.

In one embodiment, free or unbound PEG is a linear polymer terminated at each end with hydroxyl groups:

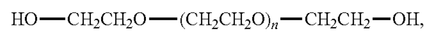

wherein "n" ranges from zero to about 4,000, or more specifically, from about 10 to about 2000, or more specifically, from about 50 to about 1000, or more specifically, from about 100 to about 500, or more specifically, from about 200 to about 250.

The above polymer, alpha-, omega-dihydroxylpoly(ethylene glycol), can be represented in a brief form as HO-PEG-OH where it is understood that the -PEG- symbol can represent the following structural unit:

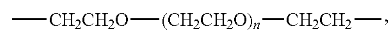

wherein "n" is as defined above.

In another embodiment, the PEG is methoxy-PEG-OH, or mPEG in brief, in which one terminus is the relatively inert methoxy group, while the other terminus is a hydroxyl group. The structure of an mPEG is given below:

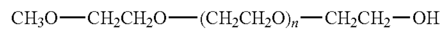

wherein "n" ranges from zero to about 4,000, or more specifically, from about 10 to about 2000, or more specifically, from about 50 to about 1000, or more specifically, from about 100 to about 500, or more specifically, from about 200 to about 250.

In one embodiment, multi-armed or branched PEG molecules, such as those described in U.S. Pat. No. 5,932,462, can be used as the PEG polymer. For example, PEG can have the structure:

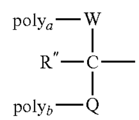

wherein:

$poly_a$ and $poly_b$ are PEG backbones (either the same or different), such as methoxy poly(ethylene glycol);

R" is a nonreactive moiety, such as H, methyl or a PEG backbone; and

W and Q are nonreactive linkages.

In one embodiment, the branched PEG polymer is methoxy poly(ethylene glycol) di-substituted lysine. Depending on the specific IL-2 moiety used, the reactive ester functional group of the di-substituted lysine may be further modified to form a functional group suitable for reaction with the target group within the IL-2 moiety.

In addition, the PEG can comprise a forked PEG. An example of a forked PEG is represented by the following structure:

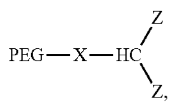

wherein: X is a spacer moiety of one or more atoms and each Z is an activated terminal group linked to CH by a chain of atoms of defined length. International Patent Application Publication WO 99/45964 discloses various forked PEG structures suitable for present use. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages in the polymer, including any of the above-described polymers. For example, PEG can be prepared with ester linkages in the polymer that are subject to hydrolysis. As shown below, this hydrolysis results in cleavage of the polymer into fragments of lower molecular weight:

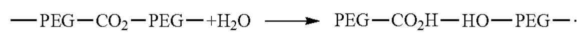

Other hydrolytically degradable linkages, useful as a degradable linkage within a polymer backbone and/or as a degradable linkage to an IL-2 moiety, include, but are not limited to, carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

Such optional features of the conjugate, i.e., the introduction of one or more degradable linkages into the polymer chain or to the IL-2 moiety, may provide for additional control over the final desired pharmacological properties of the conjugate upon administration. For example, a large and relatively inert conjugate (i.e., having one or more high molecular weight PEG chains attached thereto, for example, one or more PEG chains having a molecular weight greater than about 100,000, or more specifically, greater than about 80,000, or even more specifically, greater than about 60,000, wherein the conjugate possesses essentially no bioactivity) may be administered, which is released to generate a bioactive conjugate possessing a portion of the original PEG chain. In this way, the properties of the conjugate can be more effectively tailored to balance the bioactivity of the conjugate over time.

The water-soluble polymer associated with the conjugate can also be "releasable." That is, the water-soluble polymer releases (either through hydrolysis, enzymatic processes, catalytic processes or otherwise), thereby resulting in the unconjugated IL-2 moiety. In some instances, releasable polymers detach from the IL-2 moiety in vivo without leaving any fragment of the water-soluble polymer. In other instances, releasable polymers detach from the IL-2 moiety in vivo leaving a relatively small fragment (e.g., a succinate tag) from the water-soluble polymer. An exemplary releasable polymer includes one that attaches to the IL-2 moiety via a carbonate linkage.

As described herein, an IL-2 conjugate comprises one or more water-soluble polymers covalently attached to an IL-2 moiety. Typically, for any given conjugate, there are one to eight water-soluble polymers covalently attached to one or more moieties having IL-2 activity. In one embodiment, the conjugate has 1, 2, 3, 4, 5, or 6 water-soluble polymers individually attached to an IL-2 moiety. Any given water-soluble polymer may be covalently attached to either an amino acid of the IL-2 moiety, or, when the IL-2 moiety is (for example) a glycoprotein, to a carbohydrate of the IL-2 moiety. Attachment to a carbohydrate may be carried out, e.g., using metabolic functionalization employing sialic acid-azide chemistry [Luchansky et al. (2004) *Biochemistry* 43(38):12358-12366] or other suitable approaches such as the use of glycidol to facilitate the introduction of aldehyde groups [Heldt et al. (2007) *European Journal of Organic Chemistry* 32:5429-5433].

The particular linkage within the moiety having IL-2 activity and the polymer depends on a number of factors. Such factors include, but are not limited to, the particular linkage chemistry employed, the particular IL-2 moiety, the available functional groups within the IL-2 moiety (either for attachment to a polymer or conversion to a suitable attachment site), and the presence of additional reactive functional groups within the IL-2 moiety.

The conjugates of the invention can be, although not necessarily, prodrugs, meaning that the linkage between the polymer and the IL-2 moiety is releasable to allow release of the parent moiety. Exemplary releasable linkages include, but are not limited to, carboxylate ester, phosphate ester, thiol ester, anhydrides, acetals, ketals, acyloxyalkyl ether, imines, orthoesters, peptides and oligonucleotides. Such linkages can be readily prepared by appropriate modification of either the IL-2 moiety (e.g., the carboxyl group C terminus of the protein, or a side chain hydroxyl group of an amino acid such as serine or threonine contained within the protein, or a similar functionality within the carbohydrate) and/or the polymeric reagent using coupling methods commonly employed in the art. In one embodiment, the releaseable linkages are readily formed by reaction of a suitably activated polymer with a non-modified functional group contained within the moiety having IL-2 activity.

Alternatively, a hydrolytically stable linkage, such as an amide, urethane (also known as carbamate), amine, thioether (also known as sulfide), or urea (also known as carbamide) linkage can also be employed as the linkage for coupling the IL-2 moiety. In one embodiment, the hydrolytically stable linkage is an amide. In one approach, a water-soluble polymer bearing an activated ester can be reacted with an amine group on the IL-2 moiety to thereby result in an amide linkage.

The conjugates (as opposed to an unconjugated IL-2 moiety) may or may not possess a measurable degree of IL-2 activity. That is to say, a polymer-IL-2 moiety conjugate disclosed herein will possesses anywhere from about 0.1% to about 100% of the bioactivity of the unmodified parent IL-2 moiety. In some instances, the polymer-IL-2 moiety conjugates may have greater than 100% bioactivity of the unmodified parent IL-2 moiety. In one embodiment, conjugates possessing little or no IL-2 activity contain a hydrolyzable linkage connecting the polymer to the moiety, so that regardless of the lack (or relatively lack) of activity in the conjugate, the active parent molecule (or a derivative thereof) is released upon aqueous-induced cleavage of the hydrolyzable linkage. Such activity may be determined using a suitable in-vivo or in-vitro model, depending upon the known activity of the particular moiety having IL-2 activity employed.

For conjugates possessing a hydrolytically stable linkage that couples the moiety having IL-2 activity to the polymer, the conjugate typically possess a measurable degree of bioactivity. For instance, such conjugates are typically characterized as having a bioactivity satisfying one or more of the following percentages relative to that of the unconjugated IL-2 moiety: at least about 2%, at least about 5%, at least about 10%, at least about 15%, at least about 25%, at least about 30%, at least about 40%, at least about 50%, at least about 60%, at least about 80%, at least about 85%, at least about 90%, at least about 95%, at least about 97%, at least about 100%, and more than 105% (when measured in a suitable model, such as those well known in the art). In one embodiment, conjugates having a hydrolytically stable linkage (e.g., an amide linkage) will possess at least some degree of the bioactivity of the unmodified parent moiety having IL-2 activity.

Exemplary conjugates are described in more detail below. Typically, such an IL-2 moiety is expected to share (at least in part) a similar amino acid sequence as the sequence provided in SEQ ID NO: 1. Thus, while reference will be made to specific locations or atoms within SEQ ID NO: 1, such a reference is for convenience only and one having ordinary skill in the art can readily determine the corresponding location or atom in other moieties having IL-2 activity. In particular, the description provided herein for native human IL-2 is often applicable to fragments, deletion variants, substitution variants or addition variants of any of the foregoing.

Amino groups on IL-2 moieties provide a point of attachment between the IL-2 moiety and the water-soluble polymer. Using the amino acid sequence provided in SEQ ID NO: 1, it is evident that there are several lysine residues in each having an s-amino acid that may be available for conjugation. Further, the N-terminal amine of any protein can also serve as a point of attachment.

Conjugation of a polymeric reagent to an amino group of an IL-2 moiety can be accomplished by a variety of techniques. In one approach, an IL-2 moiety can be conjugated to a polymeric reagent functionalized with a succinimidyl derivative (or other activated ester group, wherein approaches similar to those described for these alternative activated ester group-containing polymeric reagents can be used). In this approach, the polymer bearing a succinimidyl derivative can be attached to the IL-2 moiety in an aqueous media at a pH of 7 to 9.0, although using different reaction conditions (e.g., a lower pH such as 6 to 7, or different temperatures and/or less than 15° C.) can result in the attachment of the polymer to a different location on the IL-2 moiety. In addition, an amide linkage can be formed by reacting an amine-terminated nonpeptidic, water-soluble polymer with an IL-2 moiety bearing an activating a carboxylic acid group.

In one embodiment, an IL-2 conjugate comprises a releasable linkage wherein an IL-2 moiety is conjugated to one or more PEG polymeric agents having the following structure:

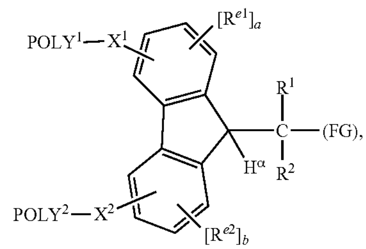

wherein:

$POLY^1$ is a first water-soluble polymer;

$POLY^2$ is a second water-soluble polymer;

$X^1$ is a first spacer moiety;

$X^2$ is a second spacer moiety;

$H_\alpha$ is an ionizable hydrogen atom;

$R^1$ is H or $C_{1-6}$alkyl;

$R^2$ is H or $C_{1-6}$alkyl;

a is either zero or one;

b is either zero or one;

$R_{e1}$, when present, is a first electron altering group;

$R^{e2}$, when present, is a second electron altering group; and (FG) is a functional group capable of reacting with an amino group of an active agent to form a releasable linkage, such as a carbamate linkage.

In one embodiment, an IL-2 conjugate comprises a releasable linkage wherein an IL-2 moiety is conjugated to one or more PEG polymeric agents having the following structure:

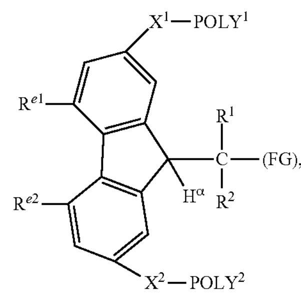

wherein each of $POLY^1$, $POLY^2$, $X^1$, $X^2$, $R^1$, $R^2$, $H_\alpha$ and (FG) is as previously defined, and $R^{e1}$ is a first electron altering group; and $R^{e2}$ is a second electron altering group.

In one embodiment, an IL-2 conjugate comprises a releasable linkage wherein an IL-2 moiety is conjugated to one or more PEG polymeric agents having the following structure:

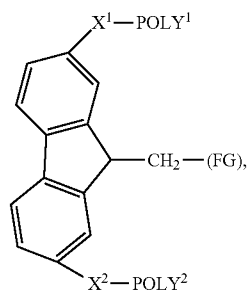

wherein each of $POLY^1$, $POLY^2$, $X^1$, $X^2$ and (FG) is as previously defined.

In one embodiment, an IL-2 conjugate comprises a releasable linkage wherein an IL-2 moiety is conjugated to one or more PEG polymeric agents having the following structure:

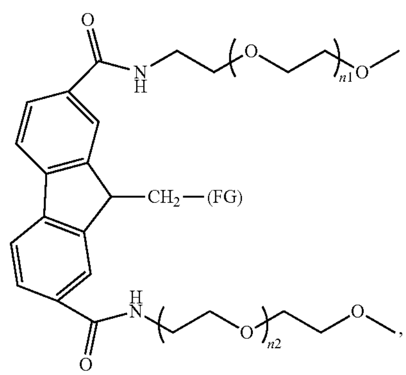

wherein (FG) is as previously defined; and each of n1 and n2 is independently selected from 1-1500. In one embodiment, each of n1 and n2 is independently selected from 10-1000. In one embodiment, each of n1 and n2 is independently selected from 100-500. In one embodiment, each of n1 and n2 is independently selected from 150-300. In one embodiment, each of n1 and n2 is independently selected from 200-250. In another embodiment, each of n1 and n2 is independently about 235.

In one embodiment, an IL-2 conjugate comprises a releasable linkage wherein an IL-2 moiety is conjugated to one or more PEG polymeric agents having the following structure:

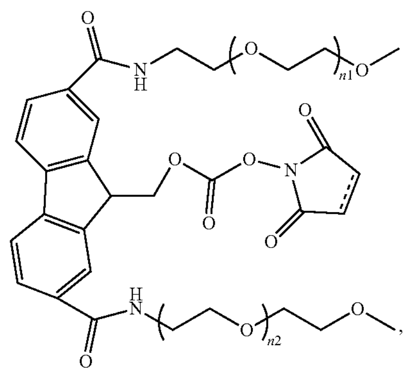

wherein the dashed bond "=====" is an optional double bond; and each of n1 and n2 is independently selected from 1-2000. In one embodiment, each of n1 and n2 is independently selected from 10-1000. In one embodiment, each of n1 and n2 is independently selected from 100-500. In one embodiment, each of n1 and n2 is independently selected from 150-300. In one embodiment, each of n1 and n2 is independently selected from 200-250. In another embodiment, each of n1 and n2 is independently about 235.

In one embodiment, an IL-2 conjugate comprises a releasable linkage wherein an IL-2 moiety is conjugated to one or more PEG polymeric agents having the following structure:

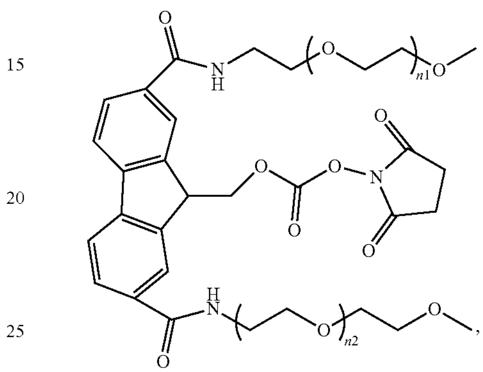

wherein each of n1 and n2 is independently selected from 1-1500. In one embodiment, each of n1 and n2 is independently selected from 10-1000. In one embodiment, each of n1 and n2 is independently selected from 100-500. In one embodiment, each of n1 and n2 is independently selected from 150-300. In one embodiment, each of n1 and n2 is independently selected from 200-250. In another embodiment, each of n1 and n2 is independently about 235.

In one embodiment, an IL-2 conjugate comprises a releasable linkage wherein an IL-2 moiety is conjugated to one or more PEG polymeric agents having the following structure:

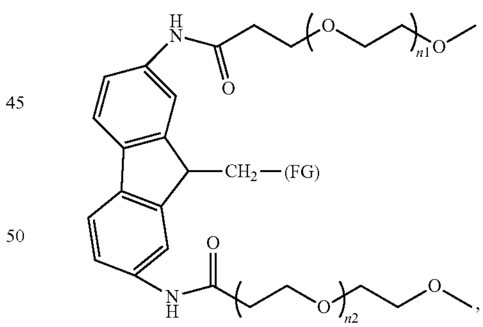

wherein (FG) is as previously defined; and each of n1 and n2 is independently selected from 1-1500. In one embodiment, each of n1 and n2 is independently selected from 10-1000. In one embodiment, each of n1 and n2 is independently selected from 100-500. In one embodiment, each of n1 and n2 is independently selected from 150-300. In one embodiment, each of n1 and n2 is independently selected from 200-250. In another embodiment, each of n1 and n2 is independently about 235.

In one embodiment, an IL-2 conjugate comprises a releasable linkage wherein an IL-2 moiety is conjugated to one or more PEG polymeric agents having the following structure:

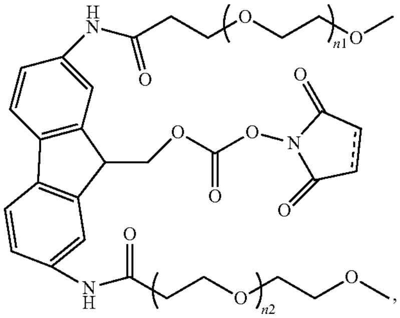

wherein the dashed bond "$\text{=====}$" is an optional double bond; and each of n1 and n2 is independently selected from 1-1500. In one embodiment, each of n1 and n2 is independently selected from 10-1000. In one embodiment, each of n1 and n2 is independently selected from 100-500. In one embodiment, each of n1 and n2 is independently selected from 150-300. In one embodiment, each of n1 and n2 is independently selected from 200-250. In another embodiment, each of n1 and n2 is independently about 235.

In one embodiment, an IL-2 conjugate comprises a releasable linkage wherein an IL-2 moiety is conjugated to one or more PEG polymeric agents having the following structure:

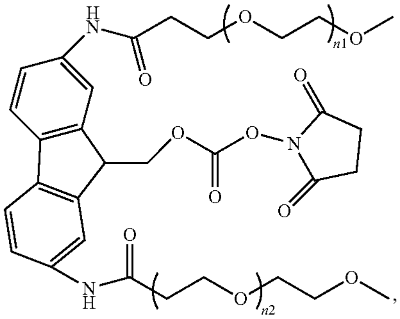

wherein each of n1 and n2 is independently selected from 1-1500. In one embodiment, each of n1 and n2 is independently selected from 10-1000. In one embodiment, each of n1 and n2 is independently selected from 100-500. In one embodiment, each of n1 and n2 is independently selected from 150-300. In one embodiment, each of n1 and n2 is independently selected from 200-250. In another embodiment, each of n1 and n2 is independently about 235.

Suitable polymeric reagents disclosed herein can be purchased from commercial sources or prepared from commercially available starting materials.

The attachment between the IL-2 moiety and the non-peptidic water-soluble polymer can be direct, wherein no intervening atoms are located between the IL-2 moiety and the polymer, or indirect, wherein one or more atoms are located between the IL-2 moiety and the polymer. With respect to the indirect attachment, a "spacer moiety" serves as a linker between the residue of the IL-2 moiety and the water-soluble polymer. The one or more atoms making up the spacer moiety can include one or more of carbon atoms, nitrogen atoms, sulfur atoms, oxygen atoms, and combinations thereof. The spacer moiety can comprise an amide, secondary amine, carbamate, thioether, and/or disulfide group. In one embodiment, a spacer moiety is selected from the group consisting of —O—, —S—, —S—, —C(O)—, —C(O)—NH—, —NH—C(O)—NH—, —O—C(O)—NH—, —C(S)—, $—CH_2—$, $—CH_2—CH_2—$, $—CH_2—CH_2—CH_2—$, $—CH_2—CH_2—CH_2—CH_2—$, $—O—CH_2—$, $—CH_2—O—$, $—O—CH_2—CH_2—$, $—CH_2—O—CH_2—$, $—CH_2—CH_2—O—$, $—O—CH_2—CH_2—CH_2—$, $—CH_2—O—CH_2—CH_2—$, $—CH_2—CH_2—O—CH_2—$, $—CH_2—CH_2—CH_2—O—$, $—O—CH_2—CH_2—CH_2—CH_2—$, $—CH_2—O—CH_2—CH_2—CH_2—$, $—CH_2—CH_2—O—CH_2—CH_2—$, $—CH_2—CH_2—CH_2—O—CH_2—$, $—CH_2—CH_2—CH_2—CH_2—O—$, $—C(O)—NH—CH_2—$, $—C(O)—NH—CH_2—CH_2—$, $—CH_2—C(O)—NH—CH_2—$, $—CH_2—CH_2—C(O)—NH—$, $—C(O)—NH—CH_2—CH_2—CH_2—$, $—CH_2—C(O)—NH—CH_2—CH_2—$, $—CH_2—CH_2—C(O)—NH—CH_2—$, $—CH_2—CH_2—CH_2—C(O)—NH—$, $—C(O)—NH—CH_2—CH_2—CH_2—CH_2—$, $—CH_2—C(O)—NH—CH_2—CH_2—CH_2—$, $—CH_2—CH_2—C(O)—NH—CH_2—CH_2—$, $—CH_2—CH_2—CH_2—C(O)—NH—CH_2—$, $—CH_2—CH_2—CH_2—C(O)—NH—CH_2—CH_2—$, $—CH_2—CH_2—CH_2—CH_2—C(O)—NH—$, $—C(O)—O—CH_2—$, $—CH_2—C(O)—O—CH_2—$, $—CH_2—CH_2—C(O)—O—CH_2—$, $—C(O)—O—CH_2—CH_2—$, $—NH—C(O)—CH_2—$, $—CH_2—NH—C(O)—CH_2—$, $—CH_2—CH_2—NH—C(O)—CH_2—$, $—NH—C(O)—CH_2—CH_2—$, $—CH_2—NH—C(O)—CH_2—CH_2—$, $—CH_2—CH_2—NH—C(O)—CH_2—CH_2—$, $—C(O)—NH—CH_2—$, $C(O)—NH—CH_2—CH_2—$, $—O—C(O)—NH—CH_2—$, $—O—C(O)—NH—CH_2—CH_2—$, $NH—CH_2—$, $—NH—CH_2—CH_2—$, $—CH_2—NH—CH_2—$, $—CH_2—CH_2—NH—CH_2—$, $C(O)—CH_2—$, $—C(O)—CH_2—CH_2—$, $—CH_2—C(O)—CH_2—$, $—CH_2—CH_2—C(O)—CH_2—$, $—CH_2—CH_2—C(O)—CH_2—CH_2—$, $—CH_2—CH_2—C(O)—$, $—CH_2—CH_2—CH_2—C(O)—NH—CH_2—CH_2—NH—$, $—CH_2—CH_2—CH_2—C(O)—NH—CH_2—CH_2—NH—C(O)—$, $CH_2—CH_2—CH_2—C(O)—NH—CH_2—CH_2—NH—C(O)—CH_2—$, $—CH_2—CH_2—CH_2—C(O)—NH—CH_2—CH_2—NH—C(O)—CH_2—CH_2—$, $—O—C(O)—NH—[CH_2]_h—(OCH_2CH_2)_j—$, bivalent cycloalkyl group, —O—, —S—, an amino acid, $—N(R^6)—$, and combinations of two or more of any of the foregoing, wherein $R^6$ is H or an organic radical selected from the group consisting of alkyl, substituted alkyl, alkenyl, substituted alkenyl, alkynyl, substituted alkynyl, aryl and substituted aryl; h is zero to six; and j is zero to 20. In another embodiment, a spacer moiety is selected from the group consisting of: $—C(O)—NH—(CH_2)_{16}—NH—C(O)—$, $—NH—C(O)—NH—(CH_2)_{1-6}—NH—C(O)—$, and $—O—C(O)—NH—(CH_2)_{1-6}—NH—C(O)—$, wherein the subscript values following each methylene indicate the number of methylenes contained in the structure, e.g., $(CH_2)_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., $—(CH_2CH_2O)_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment.

Control of the desired number of polymers for any given moiety can be achieved by selecting the proper polymeric reagent, the ratio of polymeric reagent to the IL-2 moiety, temperature, pH conditions, and other aspects of the conjugation reaction. In addition, reduction or elimination of the undesired conjugates can be achieved through purification means.

For example, the polymer-IL-2 moiety conjugates can be purified to obtain/isolate different conjugated species. Specifically, the product mixture can be purified to obtain an average of anywhere from one, two, three, four, five or more PEGs per IL-2 moiety. In one embodiment, the product mixture can be purified to obtain an average of three, four, five or six PEGs per IL-2 moiety. In another embodiment, the product mixture can be purified to obtain an average of four or five PEGs per IL-2 moiety. In another embodiment, the product mixture can be purified to obtain an average of five PEGs per IL-2 moiety.

The strategy for purification of the final conjugate reaction mixture depends on a number of factors, including, for example, the molecular weight of the polymeric reagent employed, the particular IL-2 moiety, the desired dosing regimen, and the residual activity and in vivo properties of the individual conjugate(s).

If desired, conjugates having different molecular weights can be isolated using gel filtration chromatography and/or ion exchange chromatography. Gel filtration chromatography can be used to fractionate differently numbered polymer-to-IL-2 moiety ratios (e.g., 1-mer, 2-mer, 3-mer, 4-mer, 5-mer, or 6-mer, wherein "1-mer" indicates 1 polymer to IL-2 moiety, "2-mer" indicates two polymers to IL-2 moiety, and so on) on the basis of their differing molecular weights (where the difference corresponds essentially to the average molecular weight of the water-soluble polymer portion). For example, in an exemplary reaction where a 15,000 Dalton IL-2 protein is randomly conjugated to a polymeric reagent having a molecular weight of about 21,000 Daltons, the resulting reaction mixture may contain unmodified protein (having a molecular weight of about 15,000 Daltons), 1×PEG IL-2 protein (having a molecular weight of about 36,000 Daltons), 2×PEG IL-2 protein (having a molecular weight of about 57,000 Daltons), 3×PEG IL-2 protein (having a molecular weight of about 78,000 Daltons), 4×PEG IL-2 protein (having a molecular weight of about 99,000 Daltons), 5×PEG IL-2 protein (having a molecular weight of about 120,000 Daltons), and so forth.

While this approach can be used to separate PEG and other polymer-IL-2 moiety conjugates having different molecular weights, this approach is generally ineffective for separating positional isoforms having different polymer attachment sites within the IL-2 moiety. For example, gel filtration chromatography can be used to separate from each other mixtures of PEG 1-mers, 2-mers, 3-mers, 4-mers, 5-mers, and so forth, although each of the recovered conjugate compositions may contain PEG(s) attached to different reactive groups (e.g., lysine residues) within the IL-2 moiety.

Gel filtration columns suitable for carrying out this type of separation include SUPERDEX™ and SEPHADEX™ columns available from Amersham Biosciences (Piscataway, N.J.). Selection of a particular column depends on the desired fractionation range desired. Elution is generally carried out using a suitable buffer, such as phosphate or acetate. The collected fractions may be analyzed by a number of different methods, for example, (i) absorbance at 280 nm for protein content, (ii) dye-based protein analysis using bovine serum albumin (BSA) as a standard, (iii) iodine testing for PEG content, (iv) sodium dodecyl sulfate polyacrylamide gel electrophoresis (SDS PAGE), followed by staining with barium iodide, and (v) high performance liquid chromatography (HPLC).

Separation of positional isoforms can be carried out by reverse phase chromatography using a reverse phase-high performance liquid chromatography (RP-HPLC) using a suitable column (e.g., a C18 column or C3 column, available commercially from companies such as Amersham Biosciences or Vydac) or by ion exchange chromatography using an ion exchange column, e.g., a SEPHAROSE™ ion exchange column available from Amersham Biosciences. Either approach can be used to separate polymer-active agent isomers having the same molecular weight (i.e., positional isoforms).

It is to be understood that the foregoing description as well as the examples that follow are intended to illustrate and not limit the scope of the disclosure. Other aspects, advantages and modifications within the scope of the invention will be apparent to those skilled in the art to which the invention pertains.

EXPERIMENTAL

The following synthetic schemes and examples are intended to be illustrative only and not limiting in any way. Abbreviations used are those conventional in the art or the following.

ACN acetonitrile
aq. aqueous
Boc tert-butyloxycarbonyl
° C. degree celsius
CEX cation-exchange chromatography
DCC 1,3-dicyclohexylcarbodiimide
DCM dichloromethane
DMF dimethylformamide
ESI electrospray ionization
Et ethyl
EtOAc ethyl acetate
EtOH ethanol
FA formic acid
g gram(s)
h hour(s)
HCl hydrochloric acid
HOBt N-hydroxybenzotriazole
HPLC high pressure liquid chromatography
L liter
LC liquid chromatography
LC-MS liquid chromatography and mass spectrometry
M molar
MALDI matrix-assisted laser desorption ionization
Me methyl
MeCN acetonitrile
MeOH methanol
mg miligram
mmol milimole
MS mass spectrometry
min minute(s)
mL milliliter(s)
N normal
NaOH sodium Hydroxide
NHS N-hydroxysuccinimide
PG protecting group
RPLC reverse-phase liquid chromatography
RPM revolutions per minute
RRHD Rapid Resolution High Definition
RT or rt room temperature
sat. saturated
t-BuOH tert-butanol
TFA trifluoroacetic acid
uL microliter(s)
UPLC ultra performance liquid chromatography

Example 1. An IL-2 Conjugate with Five Poly(ethylene glycol) Polymers

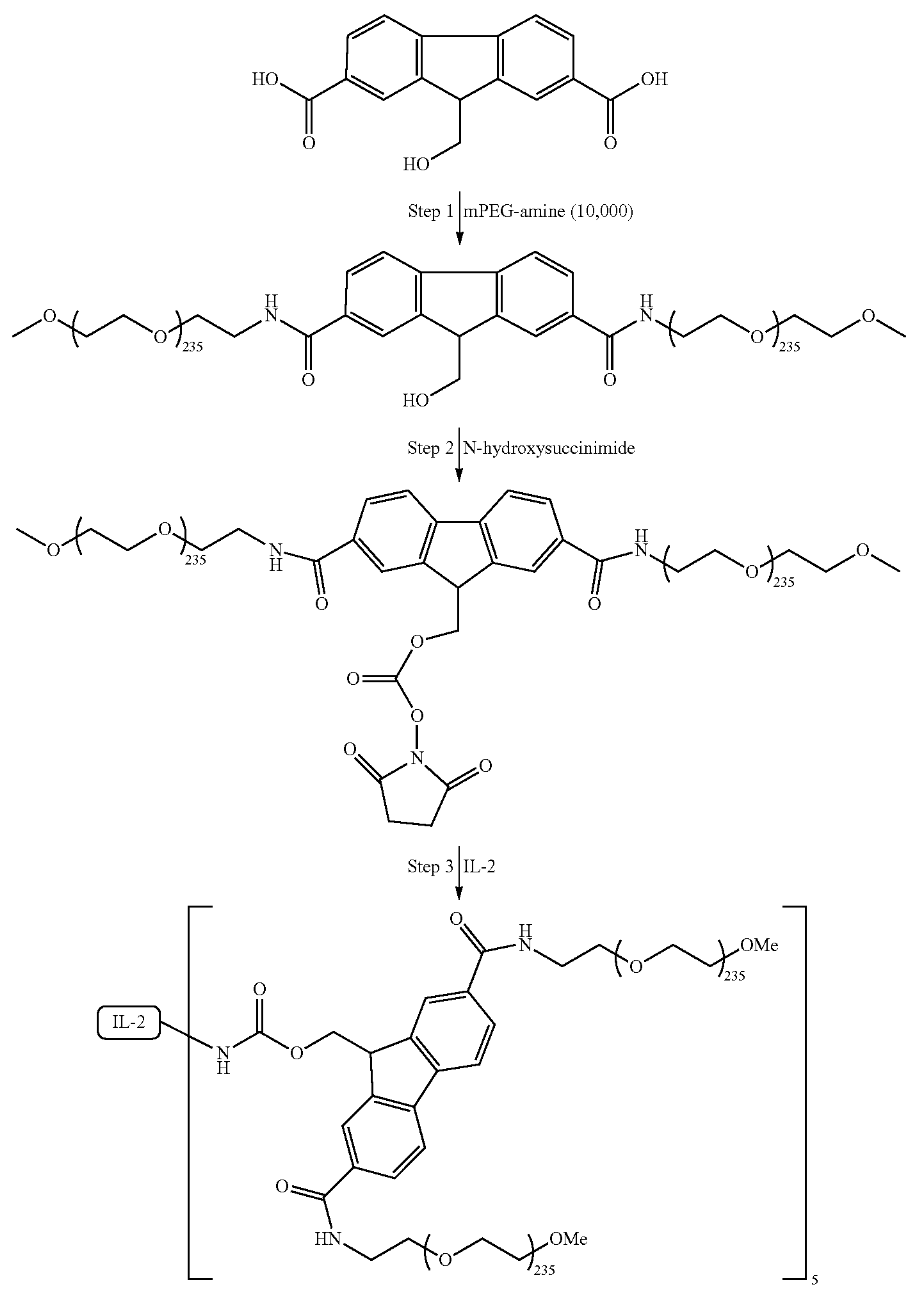

Step 1. Preparation of 9-(hydroxymethyl)-9H-fluorene-2,7-di(mPEG (10,000) amide mPEG-amine (10,000) (mPEG-amine, MW=10,427; 115 g, 11.07 mmol, 2.1 eq) was dissolved in anhydrous dichloromethane (575 mL) under a nitrogen atmosphere and stirred at RT to dissolve all solids. In a separate flask, 9-hydroxymethyl-9H-fluorene2,7-dicarboxylic acid (1 eq, 5.28 mmol, 1.5 g) and N-hydroxybenzotriazole (HOBt) anhydrous (2.1 eq, 11.08 mmol, 1.7 g) were dissolved in anhydrous DMF (45 mL). The DMF solution of 9-hydroxymethyl-9H-fluorene2,7-dicarboxylic acid was quantitatively transferred to the mPEG-amine reaction followed by addition of 1,3-dicyclohexylcarbodiimide (DCC) (2.1 eq, 11.08 mmol, 2.29 g). The reaction was stirred at RT for 18 h before the solvent was evaporated at a reduced pressure. To the compound was then added 4 L of isopropanol and heated to 50° C. to dissolve all solids. A product was precipitated upon slow cooling to RT. Eight hundred mL of diethyl ether was added and the resulting slurry was aged for 30 min at RT. The precipitated compound was filtered and washed with 7:3 isopropanol:diethyl ether and dried under vacuum with nitrogen flushing. The precipitation from isopropanol was repeated once more to afford the title compound.

Step 2. Preparation of 9-(hydroxymethyl)-9H-fluorene-2,7-di(mPEG(10,000) amide-N-hydroxysuccinimide 9-(Hydroxymethyl)-9H-fluorene-2,7-di(mPEG(10,000) amide (110.8 g, 5.25 mmol) in anhydrous ACN (1000 mL) was azeotropically distilled under reduced pressure at 25° C. on a rotary evaporator. The solid was dissolved in anhydrous DCM (742 mL), followed by the addition of triphosgene (1.5 eq, 7.88 mmol, 2.34 g). After 5 min, anhydrous pyridine (2 eq, 10.5 mmol, 0.949 mL) was added and the reaction stirred at RT for 90 min. The reaction was then concentrated using a rotary evaporator. The resulting compound was re-dissolved in anhydrous DCM (742 mL), followed by the addition of N-hydroxysuccinimide (5 eq, 26.3 mmol, 3 g, "NHS") and anhydrous pyridine (3 eq, 15.75 mmol, 1.3 mL). The reaction was stirred for 3 h at RT under nitrogen and then the solvent was removed. Isopropanol (1.1 L) was added and the resulting slurry was stirred at RT for 1 h. The compound was then filtered and the resulting wet cake was washed with 300 mL of isopropanol/diethyl ether (1:1). The resulting compound was dried under vacuum with nitrogen flushing to afford the product.

Step 3. Preparation of 5-PEGylated IL-2 Conjugate

To a reaction vessel was charged 1.190 g of IL-2 protein (SEQ ID No. 1; 410 mL of a 1.26 mg/mL solution). A reaction buffer was then added (10 mM NaOAc with 5% trehalose, pH 4.5). The reaction mixture was stirred at 125 RPM. The pH of solution was adjusted to 8.4 using a sodium borate solution (0.5M, pH 9.5). In a separate flask, 9-(hydroxymethyl)-9H-fluorene-2,7-di(mPEG(10,000) amide-N-hydroxysuccinimide (50 eq, 2.8 mmol, 94 g) was dissolved in 600 mL of water (water for injection). The hydroxysuccinimide solution was then added to the IL-2 solution in portions over one to two minutes. The pH of the reaction mixture post addition was 8.27. Additional borate buffer was added to bring the pH to 8.4. The reaction was aged for 30 min at RT and then quenched to pH 4.5 with a 2N aqueous acetic acid solution.

Example 2

Intact LC-MS was used to confirm the molecular mass for unconjugated IL-2 moiety. IL-2 samples were analyzed using a Waters Acquity UPLC system (Waters Corp., Milford, Ma) connected to a Waters Synapt G2-Si Q-TOF mass spectrometer (Waters Corp., Milford, Ma). All IL-2 samples were analyzed using a ZORBAX RRHD 300 Å StableBond C18 (2.1×100 mm, 1.8 um) (Agilent, Santa Clara, Ca) with 0.1% TFA mobile phase A and MeCN, 0.1% FA in mobile phase B. Samples were separated using a 5-95% B gradient over 8 minutes, flowing at 0.3 mL/min and a column temperature of 50° C. The online RPLC effluent was ionized by ESI in positive ion mode with the following source conditions: capillary 3.0 kV, sampling cone 40 V, source temperature 150° C., desolvation temperature 450° C., cone gas 20 L/h and a desolvation gas flow rate of 600 L/h. MaxEnt 1 was used to determine the molecular mass of IL-2 samples for all chromatographic runs. As shown in FIG. 1, the experimental intact mass matched the theoretical mass calculated from the sequence, confirming the correct sequence was isolated. The experimental mass spectral data is provided in FIG. 2.

MALDI-MS was used to confirm the molecular mass of the PEG moiety. Samples of the PEG moiety were mixed 1:1 (v/v) with a saturated solution of 9:1 (w/w) mixture of 2,5-DHB and 2-hydroxy-5-methoxybenzoic acid (Sigma-Aldrich, St. Loius, Mo). Two uLs of the resulting sample: matrix mixture were spotted in triplicate onto a 384-well MTP ground steel target plate from Bruker Corporation (Billerica, MA) and allowed to dry at ambient conditions. All samples were analyzed using Bruker RapiFlex MALDI-TOF (Billerica, Massachusetts). All spectra were acquired in linear positive ion mode by summing 3000 laser shots, 50% laser power and randomly walking over the dried sample spot. Spectra were processed and analyzed with FlexAnalysis 4.0 software.

Intact MALDI-MS was used to determine the degree of PEGylation for IL-2 post-conjugation. Samples of PEGylated IL-2 conjugates were collected in fractions from CEX purification and spun concentrated approximately 5× to 10× using Amicon Ultra 0.5 mL spin filters with a 10 K nominal molecular weight limit (Sigma-Aldrich, St. Louis MO). Concentrated samples were mixed 2:1 (v/v) with a MALDI matrix solution comprised of 10 mg/mL 2',6'-dihydroxyacetophenone (99.0% Sigma-Aldrich, St. Louis MO) in 50:50 MeCN:0.1% TFA. Two uLs of the resulting sample:matrix mixture were spotted in triplicate onto a 384-well MTP Anchorchip target plate from Bruker Corporation (Billerica, MA) and allowed to dry at ambient conditions. All samples were analyzed using Bruker RapiFlex MALDI-TOF (Billerica, Massachusetts). All spectra were acquired in linear positive ion mode by summing 30000 laser shots, 100% laser power and randomly walking over the dried sample spot. Spectra were processed and analyzed with FlexAnalysis 4.0 software. By using the experimental masses of the PEG moiety and IL-2, one can calculate the theoretical masses for IL-2 with 1-5 conjugated PEG moieties (i.e. IL-2 MW+(n*PEG MW)=conjugate MW). Using this equation the 5× PEGylated IL-2 molecular weight was calculated to be 121 kDa. With this molecular weight, MALDI-MS was used to identify CEX fractions that contained principally 5× PEGylated IL-2, as shown in FIG. 3.

Example 3

Peptide maps for IL-2 and 5× PEGylated IL-2 conjugates were generated by Glu-C digestion. Specifically, sequencing grade Glu-C (Promega Corp., Madison, WI) was prepared in a 10 mM ammonium acetate buffer at pH 4.5, to which was added 50:1 sample:protease molar ratio and incubated overnight at 37° C. with shaking at 500 rpm. The following morning, samples of digested IL-2 and PEGylated IL-2 conjugates were mixed with a 5 mg/mL solution of α-cyano-4-hydroxycinnamic acid (99.0% Sigma-Aldrich, St. Louis MO) in 50:50 MeCN:0.1% TFA. Two uLs of the resulting sample:matrix mixture were spotted in triplicate onto a 384-well MTP Anchorchip target plate from Bruker Corporation (Billerica, MA) and allowed to dry at ambient conditions. All samples were analyzed using Bruker RapiFlex MALDI-TOF (Billerica, Massachusetts). All spectra were acquired in linear positive ion mode by summing 6000 laser shots, 30% laser power and randomly walking over the dried sample spot. Spectra were processed and analyzed with FlexAnalysis 4.0 software and peptide maps were generated with BioTools 2.2. By comparing every identified peptide head-to-head between IL-2 and 5×PEGylated IL-2 conjugates, two peptides (20-51 & 95-105) were not observed for PEG-IL-2, suggesting that these peptides had been modified and shifted to a much higher m/z as a result. This indicates that lysines 31, 34, 42, 47 and 96 within these peptides were conjugated to PEG. The majority of the identified sites are at the IL-2a receptor interface. Data is shown in FIG. 4.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A process for preparing a conjugate of an interleukin-2 (IL-2) moiety comprising:

providing a water solution comprising an IL-2 moiety comprising the amino acid sequence set forth in SEQ ID NO: 1 and adding PEG fluorene NHS ester having the following formula:

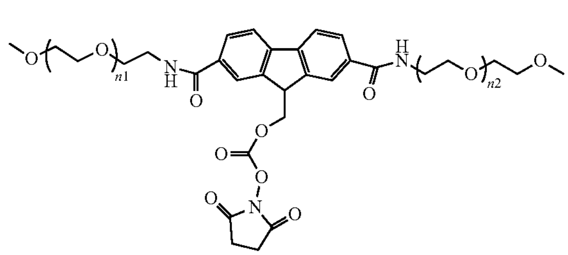

wherein each of n1 and n2 is independently selected from 150-300 in a water solution to react with the IL-2 moiety to form an IL-2 conjugate, in which the IL-2 conjugate comprises five poly(ethylene glycol) polymers each of which is covalently attached to an amino group of a lysine residue of the IL-2 moiety in a releasable linkage; and wherein the conjugation reaction is carried out at a pH of about 8.4.

2. The process of claim 1, wherein each of n1 and n2 is independently selected from 200-250.

SEQUENCE LISTING

```
<160> NUMBER OF SEQ ID NOS: 1

<210> SEQ ID NO 1
<211> LENGTH: 132
<212> TYPE: PRT
<213> ORGANISM: Homo sapiens

<400> SEQUENCE: 1

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

3. The process of claim 1, wherein the PEGylating agent is a PEG fluorene NHS ester having the following formula:
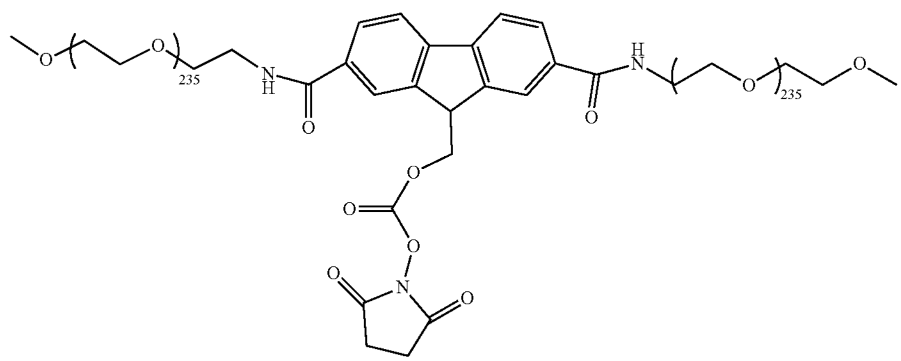
* * * * *